United States Patent
Gu et al.

(10) Patent No.: US 10,519,084 B2
(45) Date of Patent: Dec. 31, 2019

(54) CONVERSION OF NATURAL GAS INTO CLEAN LIQUID FUELS

(71) Applicants: Wichita State University, Wichita, KS (US); Farshad Houtaham, Wichita, KS (US)

(72) Inventors: Shuang Gu, Wichita, KS (US); Farshad Houtaham, Wichita, KS (US)

(73) Assignees: Wichita State University, Wichita, KS (US); Farshad Houtaham, Wichita, KS (US)

( * ) Notice: Subject to any disclaimer, the term of this patent is extended or adjusted under 35 U.S.C. 154(b) by 0 days.

(21) Appl. No.: 15/789,743

(22) Filed: Oct. 20, 2017

(65) Prior Publication Data
US 2018/0111888 A1    Apr. 26, 2018

Related U.S. Application Data

(60) Provisional application No. 62/410,596, filed on Oct. 20, 2016.

(51) Int. Cl.
| | |
|---|---|
| *C07C 29/09* | (2006.01) |
| *C07C 51/285* | (2006.01) |
| *C07C 67/40* | (2006.01) |
| *C25B 1/30* | (2006.01) |
| *B01J 19/24* | (2006.01) |
| *B01J 19/12* | (2006.01) |

(52) U.S. Cl.
CPC ............ *C07C 29/09* (2013.01); *B01J 19/122* (2013.01); *B01J 19/127* (2013.01); *B01J 19/24* (2013.01); *C07C 51/285* (2013.01); *C07C 67/40* (2013.01); *C25B 1/30* (2013.01); *B01J 2219/0875* (2013.01); *B01J 2219/0892* (2013.01); *B01J 2219/12* (2013.01); *B01J 2219/24* (2013.01); *B01J 2219/32286* (2013.01); *B01J 2219/32466* (2013.01)

(58) Field of Classification Search
CPC ....... C07C 29/09; C07C 51/285; C07C 67/40; B01J 19/127; B01J 19/122; C25B 1/30
See application file for complete search history.

(56) References Cited

U.S. PATENT DOCUMENTS

| | | | | |
|---|---|---|---|---|
| 3,983,010 | A | * | 9/1976 | Rauch ..................... C07C 51/44 203/15 |
| 4,792,620 | A | * | 12/1988 | Paulik ................. B01J 31/0231 560/232 |
| 2012/0203035 | A1 | * | 8/2012 | Lopez-Sanchez ...... C07C 29/48 568/910 |

OTHER PUBLICATIONS

Norskov et al, Nature Chemistry, Towards the Computational Design of Solid Catalysts, 2009, 1, pp. 37-46. (Year: 2009).*
Lim et al, Chemical Communications, Highly active heterogeneous Fenton catalyst using iron oxide nanoparticles immobilized in alumina coated mesoporous silica, 2006, pp. 463-465. (Year: 2006).*
Cook, et al., "Ambient Temperature Methane Activation to Condensed Species under Cathodic Conditions", J. Electrochem. Soc., vol. 137, issue 6, Jun. 1990.
Karl W. Frese, Jr., "Partial Electrochemical Oxidation of Methane under Mild Conditions", Langmuir, vol. 7, issue 1, 1991, pp. 13-15.
Helmut Schwarz, "Chemistry with Methane: Concepts Rather than Recipes", Angew. Chem. Int. Ed., 2011, 50, 10096-10115.
Tomita, et al., "Direct Oxidation of Methane to Methanol at Low Temperature and Pressure in an Electrochemical Fuel Cell", Angew. Chem. Int. Ed., 2008, 47, 1462-1464.

* cited by examiner

*Primary Examiner* — Paul A Zucker
(74) *Attorney, Agent, or Firm* — Hovey Williams LLP

(57) ABSTRACT

Provided herein are methods and systems for converting natural gas, and specifically methane, into higher-value oxycarbon products, such as methanol, methyl formate, and formic acid. The natural gas is introduced into an aqueous solution with hydroxyl radicals and reacted in ambient conditions to form the desired products in the presence of a metal catalyst. The methods described herein overcome the "over-activation" dilemma of prior art methods that lead to the formation of undesirable carbon oxide compounds. Methods and apparatus for forming hydrogen peroxide via electrolysis and for forming hydroxyl radicals from the hydrogen peroxide via reaction with ferrous ions are also provided.

10 Claims, 6 Drawing Sheets

CONVERSION OF NATURAL GAS INTO CLEAN LIQUID FUELS

CROSS-REFERENCE TO RELATED APPLICATIONS

The present application claims the priority benefit of U.S. Provisional Patent Application Ser. No. 62/410,596, filed Oct. 20, 2016, entitled CONVERSION OF NATURAL GAS INTO CLEAN LIQUID FUELS, incorporated by reference in its entirety herein.

BACKGROUND OF THE INVENTION

Field of the Invention

The present invention is generally directed to processes and systems for upgrading natural gas to value-added oxycarbon products.

Description of Related Art

The production of natural gas in the U.S. is projected to increase by 30% and 55% in 2025 and 2040, respectively, mainly thanks to the recent explosive growth of shale gas exploration. In fact, the supply of natural gas in U.S. will quickly exceed the domestic consumption. As a result, the (crude) oil-to-(natural) gas price ratio is expected to increase from 2.5 in 2015 to 3.1 and 4.9 in 2025 and 2040, respectively. Oxycarbon products are much more valuable than the crude oil. The prices of oxycarbon products are around 10-20 times as much as that of natural gas based on the same carbon molarity. For example, the prices of methanol ($CH_3OH$), formic acid ($HCOOH$), and methyl formate ($HCOOCH_3$) are 7.9, 15.7, and 17.5 times as much as that of natural gas, respectively, based on the same carbon molarity.

High abundance and low cost of natural gas provide a clear motivation and unique opportunity for upgrading methane, the dominant component of natural gas, to value-added and handling-convenient oxycarbon products. Note that the natural gas can be liquefied, called liquefied natural gas (LNG), via a cooling process at a very low temperature (typically, −160° C.). And thus, the handling and transportation of LNG are rather costly, largely because LNG demands the expensive cryogenic conditions for all the time to maintain its liquid form. Compared with LNG, converting natural gas to oxycarbon products is a preferred route.

Prior art methods for producing oxycarbon products, such as methanol, include thermal synthesis and electrochemical methods. Thermal synthesis requires thermal activation of C—H bonds in methane, which requires high temperature (typically, 700-1,000° C.) and the presence of metal-based heterogeneous catalyst. Electrochemical methods include anodic (direct oxidation) and cathodic (indirect oxidation) techniques. However, the products or intermediates using the electrochemical techniques are kinetically more prone to further oxidation than the starting methane molecules with its thermodynamically-strong C—H bonds, which presents an "over-oxidation" challenge. As a result, the undesired carbon oxide products (CO and $CO_2$ with deeper oxidation depth) are often the major products, instead of the desired oxycarbon products such as methanol or formic acid.

What is needed is a process for converting natural gas to oxycarbon products while avoiding problems associated with the "over-activation" dilemma.

SUMMARY OF THE INVENTION

The facilitation phenomenon of metal surfaces is the key to methane activation by hydroxyl radicals (OH.), which helps to resolve the problems associated with the "over-activation" dilemma when converting methane to valuable oxycarbon products. Notably, the adsorption of $CH_4/CH_3$. (methyl radical) on the metal surface is believed to drastically lower the activation energy of methane reacting with hydroxyl radicals, which also explains why the oxycarbon products with lower C—H bond strengths can survive in the hydroxyl radical-containing environment without further reacting to form the undesirable carbon oxides. Additionally, the adsorption energies of the oxycarbon products on the metal catalyst are generally different from that of $CH_4/CH_3$-, and thus the adsorption of $CH_4/CH_3$— is more favored on the metal surface than that of the products under the test conditions. Based on this activation mechanism, provided herein are improved methods and systems for upgrading natural gas to value-added oxycarbon products in aqueous systems under ambient conditions.

In one embodiment of the present invention, there is provided a method of converting methane to an oxycarbon product. The method comprises dissolving methane in an aqueous solution comprising hydroxyl radicals and reacting the methane and hydroxyl radicals in the presence of a metal catalyst having a $CH_3$.-M binding energy of less than about 0 eV to produce the oxycarbon product.

In another embodiment, there is provided a system for converting methane to an oxycarbon product. The system comprises an aqueous solution comprising hydrogen peroxide and ferrous ions, a source of methane adapted to dissolve the methane in the solution, and a metal catalyst having a $CH_3$.-M binding energy of less than about 0 eV present in the aqueous solution and adapted to convert the methane into the oxycarbon product.

DETAILED DESCRIPTION OF PREFERRED EMBODIMENTS

Figure 1:
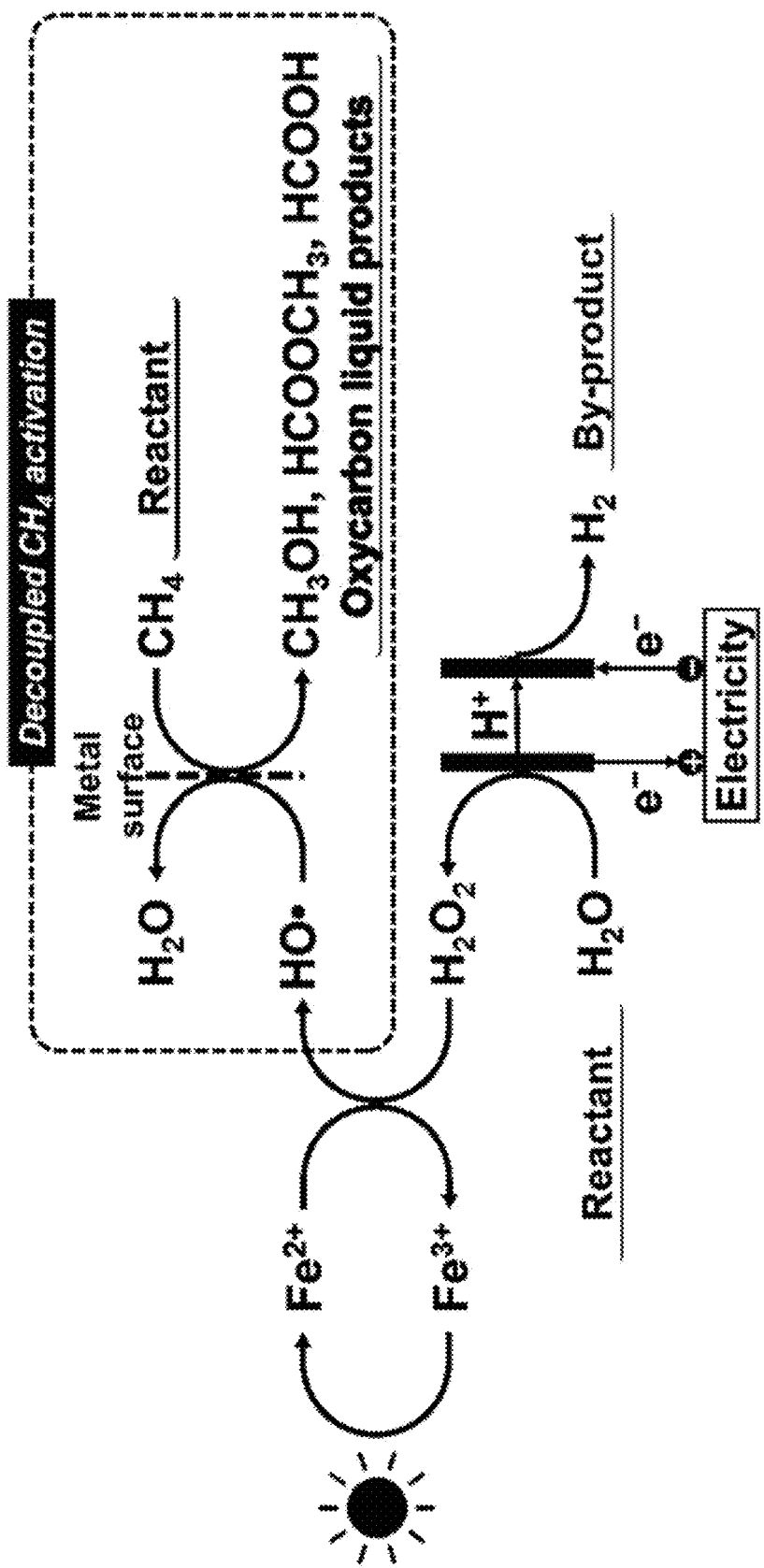
FIG. 1 is a schematic diagram of the reaction mechanisms in accordance with one embodiment of the present invention.

Embodiments of the present invention are directed to methods of converting methane to oxycarbon product and systems for implementing these methods. Methane activation (i.e., to methyl radical) and conversion to desirable products can be improved over prior art methods due to metal-surface facilitation using hydroxyl radicals as an activating agent in aqueous systems. Metal-surface facilitation enables a desired decoupling design, which provides freedom in controlling the methane activation and product distribution. In one or more embodiments, the method comprises converting methane to an oxycarbon product by dissolving the methane in an aqueous solution comprising hydroxyl radicals and reacting the methane and hydroxyl radicals in the presence of a metal catalyst to produce the oxycarbon product. In certain embodiment, the aqueous solution may further comprise hydrogen peroxide and a source of ferrous ($Fe^{2+}$) ions, which react with each other to provide a reliable supply of hydroxyl radicals.

Advantageously, the methods described herein, and particularly the dissolving and reacting steps noted above, can be effectively performed under ambient conditions and still achieve a high level of desirable oxycarbon products. As used herein, the term "ambient conditions" refers to the prevailing and uncontrolled pressure, temperature, humidity, and atmospheric (e.g., $O_2$, $CO_2$, $N_2$, etc.) conditions in a room or environment where the reaction is taking place. This is particularly advantageous over prior art methane upgrade methods that require high temperatures and pressures, which increases the complexity and cost of such methods. In certain embodiments, the dissolving and/or reacting steps are performed at a temperature of less than about 50° C., preferably less than about 40° C., and more preferably less than about 35° C. In certain embodiments, the dissolving and/or reacting steps are performed at a temperature of about 0° C. to about 100° C., preferably about 10° C. to about 50° C., and more preferably about 20° C. to about 25° C. In certain embodiments, the dissolving and/or reacting steps are performed at a pressure of less than about 10 bar, preferably less than about 5 bar, and more preferably less than about 2 bar. In certain embodiments, the dissolving and/or reacting steps are performed at a pressure of about 0.1 bar to about 10 bar, preferably about 0.5 bar to about 5 bar, and more preferably about 0.7 bar to about 2 bar. In a particularly preferred embodiment, the dissolving and/or reacting steps are performed at a pressure of about 1 bar. Additionally, the dissolving and/or reacting steps can be performed without introduction of an external electrical charge to convert the methane to oxycarbon products, which is a particular advantage over prior art electrochemical methods.

The metal catalyst may be any of a variety of metal catalysts, so long as the catalyst allows for the production of oxycarbon products over the less desirable carbon oxides. In certain embodiments, the metal catalyst comprises a metal selected from the group consisting of platinum, rhenium, palladium, copper, gold, iridium, ruthenium, silver, oxides thereof, combinations thereof, and alloys thereof. In certain embodiments, the metal catalyst is in elemental form and does not comprise metal oxides, although in certain other embodiments, metal oxides may be present in the metal catalyst. In particularly preferred embodiments, the metal catalyst does not include or contain, and preferably excludes, cobalt phthalocyanine. In certain embodiments, the metal catalyst has a $CH_3$.–M (methane or methyl radical to metal) binding energy of less than about 0 eV, preferably less than about –0.8 eV, more preferably less than about –1.8 eV. In certain embodiments, the metal catalyst has a $CH_3$.–M binding energy of from about –10 eV to about 0 eV, preferably from about –5 eV to about –1 eV, and more preferably from about –3 eV to about –1.5 eV. However, in certain other embodiments, the metal catalyst may have a $CH_3$.–M binding energy even lower (i.e., less than about –10 eV). The metal catalyst may be provided as a solid structure comprising the metal catalyst material or as a support coated with the metal catalyst. The metal catalyst may be provided on any of a variety of known supports and be of a variety of shapes and sizes, depending on the particular application. In certain embodiments, the metal catalyst comprises a zeolite support. In certain embodiments, the metal catalyst is provided as a shaped body having a geometric shape selected from the group consisting of foils, spheres, pellets, cylinders, trilobes, quadralobes, and mixtures thereof. The metal catalyst may also be provided in the form of a mesh or gauze.

In certain embodiments, the oxycarbon product comprises one or more of an oxycarbon compound selected from the group consisting of methanol ($CH_3OH$), methyl formate ($HCOOCH_3$), formic acid (HCOOH), formaldehyde (HCHO), and mixtures thereof. However, in certain embodiments, the oxycarbon product is substantially free of aldehydes, and particularly is substantially free of formaldehyde. In certain embodiments, the oxycarbon product comprises a quantity of each of the methanol, methyl formate, and formic acid. In certain such embodiments, the methanol, methyl formate, and formic acid are present in the oxycarbon product at a molar ratio of about 1:5:15 to about 1:1:1, preferably about 1:4:8 to about 3:6:8, and more preferably about 1:3:6 to about 1:2:3. In certain preferred embodiments, the oxycarbon product is substantially free of less desirable carbon monoxide (CO). As used herein, the term "substantially free" means that the component(s) are present in the composition at a concentration of less than 1% by weight, with the total weight of the composition taken as 100% by weight. Notably, in certain embodiments, the carbon oxides and/or aldehydes are not a product of the reaction mechanisms described herein, and thus the oxycarbon product of the reaction may be substantially free of carbon oxides and/or aldehydes prior to and without the need for a separation process to remove such compounds from the oxycarbon product. In other words, the direct end product of the reaction is an oxycarbon product that is substantially free of these compounds. In one or more embodiments, the oxycarbon product may be in a liquid state, a gaseous state, or a combination (two phase), depending on the temperature, pressure, and particular composition of the oxycarbon product.

In certain embodiments, the method further comprises a step for producing hydrogen peroxide from water via electrolysis, a step for producing the hydroxyl radicals from hydrogen peroxide and ferrous ions, and/or a step for photoreducing ferric ions to ferrous ions.

A schematic diagram of an exemplary process, including each of the above listed steps, is shown in FIG. 1.

A particularly preferred embodiment of the inventive method is described in further detail below, including a detailed explanation of the reaction mechanisms involved. However, it should be understood that this explanation is provided by way of example and should not be taken as limiting upon the overall scope of the invention.

Taking $CH_3OH$ as an example, the overall reaction of an exemplary process can be written as $2CH_4+4H_2O=2CH_3OH+4H_2+O_2$, and energy inputs are electricity (for electrolysis) and sunlight (for $Fe^{2+}$ regeneration). The proposed process involves five key steps: 1) $H_2O_2$ generation from selective electrolysis; 2) hydroxyl radical creation from $H_2O_2$ catalyzed by $Fe^{2+}$ ion; 3) $CH_{3-ad}$ formation from $CH_4$ activation by OH. with metal-surface facilitation; 4) $CH_3OH$ production from $CH_{3-ad}$ with the hydroxyl radical; and 5) $Fe^{2+}$ regeneration from $Fe^{3+}$ by photo-reduction. In this process, the methane activation, $H_2O_2$ generation, and hydroxyl radical creation are physically decoupled and thus can be individually engineered. Each of these steps is shown schematically in FIG. 1, and the detailed reaction for each step is as follows:

Step 1: Hydrogen peroxide ($H_2O_2$) is first generated by selective oxidation of water.

$$2H_2O \rightarrow H_2O_2 + H_2, E° = -1.776 \text{ V(electrolytic)}$$

[Anode: $2H_2O \rightarrow H_2O_2 + 2H^+ + 2e^-$; Cathode: $2H^+ + 2e^- \rightarrow H_2$]

Or, by selective reduction of oxygen.

$$2H_2O + O_2 \rightarrow 2H_2O_2, E° = -0.534 \text{ V (electrolytic)}$$

[Anode: $2H_2O \rightarrow 4H^+ + O_2 + 4e^-$; Cathode: $2O_2 + 4H^+ + 4e^- \rightarrow 2H_2O_2$]

Step 2: Hydroxyl radical is created from $H_2O_2$ by $Fe^{2+}$ ion (Fenton reaction).

$$H_2O_2 + Fe^{2+} + H^+ + HO. + Fe^{3+} + H_2O$$

Step 3: Methyl radical is then formed from $CH_4$ by hydroxyl radical in the presence of metal catalyst surface.

$$CH_4 + HO. + M \rightarrow CH_{3-ad} - M + H_2O$$

Step 4: Methanol product ($CH_3OH$) is produced from the fast reaction between $CH_{3-ad}$ and the hydroxyl radical.

$$CH_{3-ad} - M + HO. \rightarrow CH_3OH + M$$

Step 5: Ferrous ion ($Fe^{2+}$) is then regenerated from $Fe^{3+}$ by photo-reduction reaction.

$$4Fe^{3+} + 2H_2O + h\nu \rightarrow 4Fe^{2+} + O_2 + 4H^+$$

Each of these steps will be described in further detail below. However, it should be understood that these reaction steps are provided as individual examples, and one or more steps may be omitted or substituted with other techniques to provide appropriate reactants and products for other steps.

Figure 2:
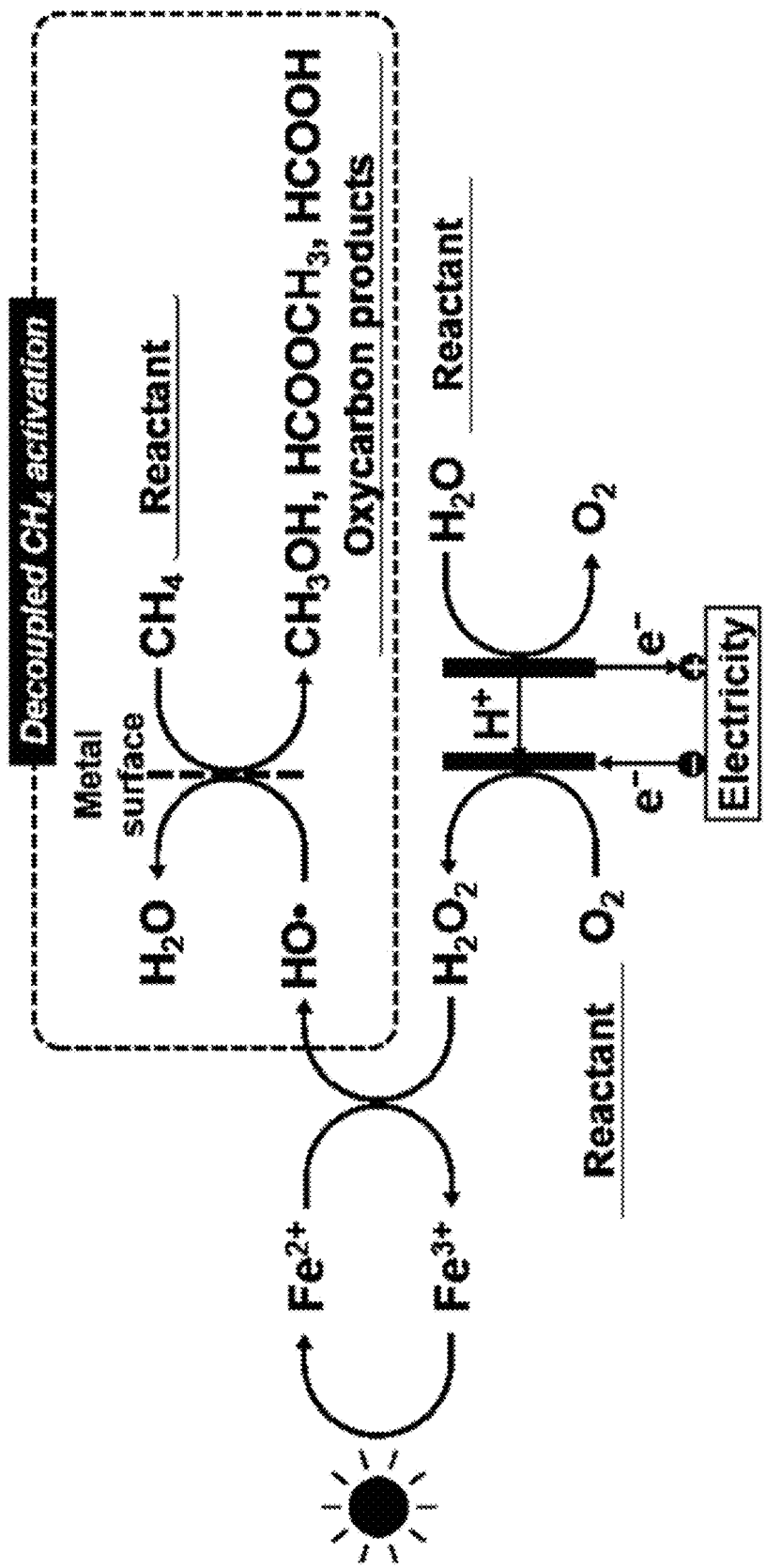
FIG. 2 is a schematic diagram of the reaction mechanisms in accordance with another embodiment of the present invention.

Step 1. Hydrogen peroxide generation by selective electrolysis of water. One of the main consumables in the process is hydrogen peroxide, which is the source for hydroxyl radicals. Therefore, in certain embodiments, a method of generating hydrogen peroxide is first provided by electrolysis of water. In certain embodiments, for example, a Pt—Hg catalyst may be used for direct electrochemical hydrogen peroxide generation in 0.1 M $HClO_4$. In certain other embodiments, gold (Au) or gold alloy can be used as a highly-selective anode catalyst for hydrogen peroxide generation. In other embodiments, an electrolysis process utilizing the combination of oxygen reduction at the cathode and oxygen evolution at the anode can be used, which is shown in the process depicted in the schematic of FIG. 2.

Step 2. Hydroxyl radical creation from $H_2O_2$ by $Fe^{2+}$ ion (Fenton reaction). Notably, once the hydrogen peroxide is provided, there is no need for further electrochemical reactions, and thus remaining steps (2 through 5) are generally performed in one or more reaction chambers separate from Step 1. In certain preferred embodiments, the hydroxyl radicals are generated from reduction of hydrogen peroxide ($H_2O_2$) by utilizing a reductive agent in the aqueous solution. For example, in certain embodiments, the hydroxyl radicals can be effectively formed from a solution comprising hydrogen peroxide and $Fe^{2+}$ (ferrous) ions via the Fenton process, wherein the ferrous ions are used to catalyze $H_2O_2$ to generate hydroxyl radicals.

Steps 3 and 4. Methyl radical formation from $CH_4$ by hydroxyl radical in the presence of metal catalyst. Methanol product ($CH_3OH$) and other oxycarbons produced from the fast reaction between adsorbed methyl radical and hydroxyl radical. Upon formation of the hydroxyl radicals, methane can be supplied to the aqueous solution, and the methane is dissolved in the aqueous solution comprising the hydroxyl ions. The presence of a metal catalyst facilitates the formation and adsorption of methyl radicals from the methane molecules in the presence of the hydroxyl radical. The adsorbed methyl radical can then quickly react with the hydroxyl radicals to form the methanol and other desirable oxycarbon products.

Step 5. Ferrous ion ($Fe^{2+}$) regeneration from ferric ion ($Fe^{3+}$) by photo-reduction reaction. Since the $Fe^{2+}$ ions are eventually consumed in oxidative environment, UV irradiation can be used to regenerate $Fe^{2+}$ from $Fe^{3+}$ via photo-reduction. Photo-reduction of $Fe^{3+}$ to $Fe^{2+}$ provides for regeneration of the Fenton reagent to constantly provide the hydroxyl radical supply to reaction system. Various dimensions of tuning (e.g., light wavelength, radiation intensity, exposure time, and temperature, and pH) can be selected to provide the appropriate rate of regeneration for the particular application. Ligands with greater ratio of oxygen to carbon ratio generally possess higher photoreduction ability.

Embodiments of the present invention are also directed to systems for converting methane to an oxycarbon product. The systems generally comprise components and apparatus for performing one or more of the method steps described above. The steps may be performed in batch or continuous systems. An exemplary system in accordance with one embodiment is shown in FIG. 3 and described in further detail below.

Figure 3:
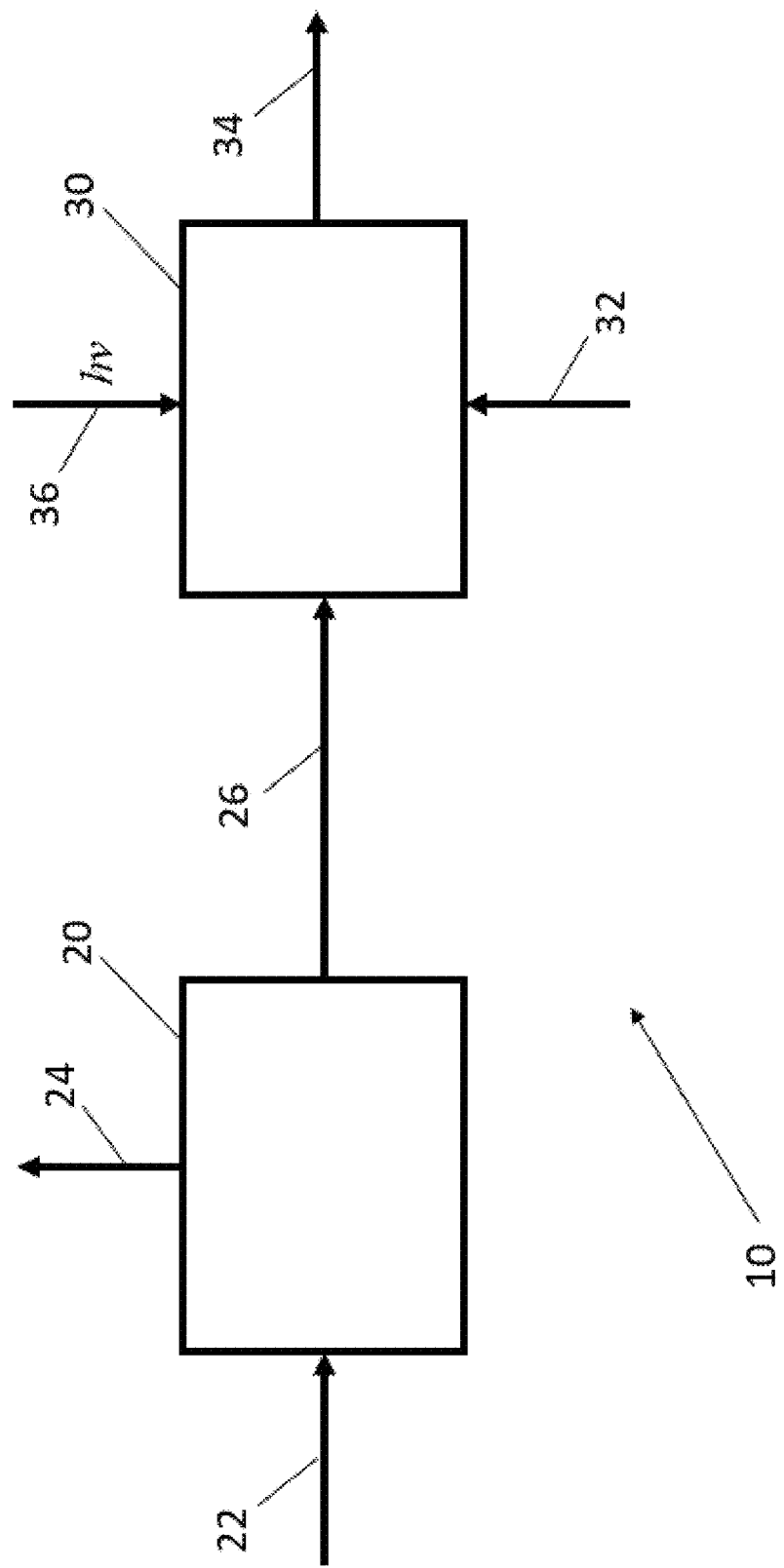
FIG. 3 is a schematic diagram of a system for converting methane to oxycarbon products in accordance with one embodiment of the present invention.

Turning to FIG. 3, a system 10 is provided for converting methane to an oxycarbon product. The system 10 generally comprises an electrolysis chamber 20 and reaction chamber 30. Electrolysis chamber 20 comprises an electrolyzer (not shown) adapted to convert water to hydrogen peroxide via water electrolysis. The electrolyzer may be any of a variety known in the art and may be adapted to oxidize the water or to reduce a source of oxygen if present. In particularly preferred embodiments, the electrolyzer comprises an anode comprising gold or a gold alloy. The source of electricity for the electrolysis may be any of a variety of electricity sources capable of supplying the necessary voltage requirements for the particularly electrolysis application. In preferred embodiments, however, the source of electricity is a renewable electricity source (e.g., wind, solar, hydroelectric). A water source 22 is adapted to provide water to electrolysis chamber 20, and a gas outlet 24 is adapted to direct hydrogen gas (as a by-product of the electrolysis) out of electrolysis chamber 20.

The solution comprising hydrogen peroxide generated by the electrolyzer is transferred to reaction chamber 30 via conduit 26. Reaction chamber 30 comprises a metal catalyst (not shown) adapted to convert the hydrogen peroxide and methane into an oxycarbon product. The metal catalyst may be any of the metal catalysts described above and may be of a variety of shapes and sizes to fit the particular application. Reaction chamber 30 may be configured to allow for the metal catalyst to be recharged or replaced as necessary without disrupting the operation of the system 10. Gas inlet 32 is adapted to provide a source of methane (e.g., natural gas) to the aqueous solution within reaction chamber 30. The amount of methane added to the aqueous solution may be varied, depending on a number of factors including reactant concentrations in the solution and desired conversion. The source of methane may be from a substantially pure methane stream (i.e., greater than 99% by weight purity) or from streams comprising methane, other hydrocarbons, and other impurities (e.g., natural gas). In certain embodiments, however, the source of methane is a gas stream comprising at least about 50% by weight, preferably at least about 75% by weight, and more preferably at least about 90% by weight of methane, with the total weight of the gas stream taken as 100% by weight.

Reaction chamber 30 further comprises a source of ferrous ions that combine with the hydrogen peroxide to provide Fenton's reagent for producing hydroxyl radicals in the solution, which converts the ferrous ions to ferric ions. The source of ferrous ions may be any number of a variety of compounds that are capable of dissolving such ions in aqueous solutions, including inorganic ferrous salts and/or organic ferrous salts. In certain embodiments, the source of ferrous ions is an iron-containing compound selected from the group consisting of $FeSO_4$ (iron(II) sulfate), $FeCl_2$ (iron(II) chloride), $FeHPO_4$, $Fe_3(PO_4)_2$, $Fe(NO_3)_2$, and $Fe(ClO_4)_2$, $Fe(CH_3COO)_2$, $Fe(C_2O_4)$, Fe-EDTA, and mixtures thereof. In a particularly preferred embodiment, the source of ferrous ions is $FeSO_4$. In certain such embodiments, the aqueous solution has a $FeSO_4$ molar concentration of about 0.05 mM to about 50 mM, preferably about 0.1 mM to about 10 mM, and more preferably about 0.25 mM to about 1 mM. In a particularly preferred embodiment, the aqueous solution has a $FeSO_4$ molar concentration of about 0.5 mM. In certain embodiments, the aqueous solution has a hydrogen peroxide molar concentration of about 1 mM to about 1000 mM, preferably about 10 mM to about 100 mM, and more preferably about 20 mM to about 50 mM. In a particularly preferred embodiment, the aqueous solution has a hydrogen peroxide molar concentration of about 25 mM. Regardless the embodiment, the source of ferrous ions is generally provided such that the solution has a molar concentration ratio of hydrogen peroxide to ferrous ions of about 1:1 to about 200:1, preferably about 10:1 to about 100:1, and more preferably about 25:1 to about 75:1. An acidic solution environment is generally required to generate hydroxyl radicals. Thus, in certain embodiments, the solution comprises an acid, such as sulfuric acid. Other organic and inorganic acids may also be used. In certain embodiments the aqueous solution has a pH of about 0 to about 6, preferably from about 1 to about 5, and more preferably from about 2.5 to about 4. In a particularly preferred embodiment, the aqueous solution has a pH of about 3. Reaction chamber 30 may further comprise a light source 36 to photoreduce the ferric ions, thereby regenerating the ferrous ions and providing a constant supply of the Fenton's reagent and hydroxyl radicals.

The methane and hydroxyl radicals react in the presence of the metal catalyst in reaction chamber 30 as described above. The oxycarbon product can then be recovered via outlet 34 and sent downstream for further processing. For example, the product may comprise multiple oxycarbon compounds and other by-products that need to be separated before use or sale. A series of separations may be required depending on the specific components and quantities in the product. For example, while the methanol may be easily separated from aqueous solutions by distillation techniques and the methyl formate may only require a simple separation because of its high boiling point (partial pressure of about 60 kPa), other components such as formic acid may require a separate and more complex separation technique.

Figure 4:
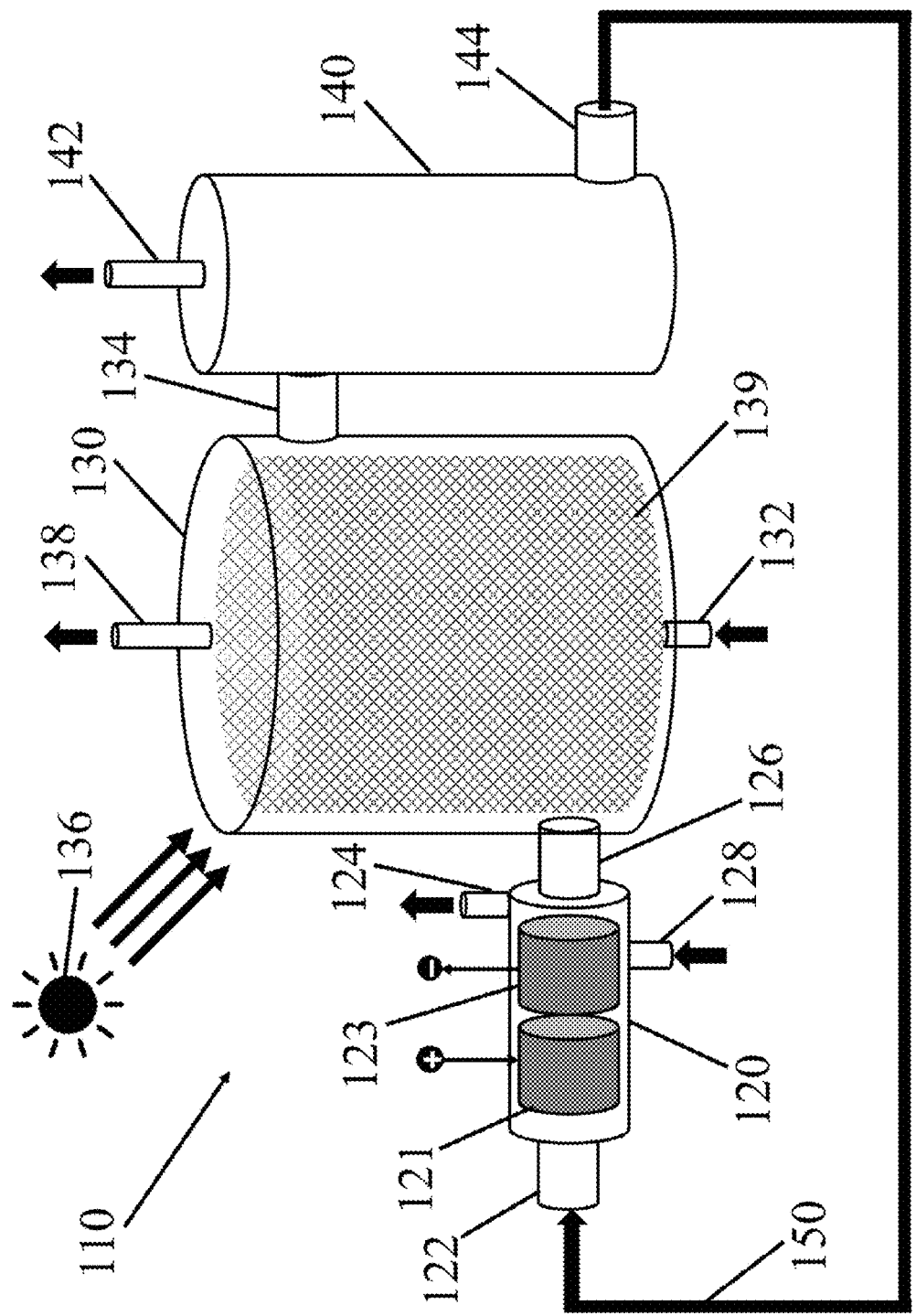
FIG. 4 is a schematic diagram of a system for converting methane to oxycarbon products in accordance with another embodiment of the present invention.

Another exemplary system in accordance with one embodiment is shown in FIG. 4 and described below. System 110 is similar to system 10 described above, with additional apparatus features shown and described below. Electrolysis chamber 120 and reaction chamber 130 are depicted in FIG. 4 as being transparent in order to show certain internal components. However, it should be understood that these units may be constructed using transparent or opaque materials within the scope of the present invention.

Turning to FIG. 4, aqueous stream 150 is fed to electrolysis chamber 120 via electrolysis inlet 122. In certain embodiments, aqueous stream 150 provides a substantially pure water supply to electrolysis chamber 120. As used herein, the term "substantially pure" means the stream comprises less than 1% by weight of dissolved or suspended particles, colloids, gases, or other impurities. However, in certain embodiments, aqueous stream 150 is a recycle stream and may comprise some amount of impurities, including unreacted reactant components and unseparated product components. Electrolysis chamber 120 comprises cathode 121 and anode 123, which operate to produce hydrogen peroxide from the water supplied by aqueous stream 150. An air stream (or other oxygen supply) may be fed into electrolysis chamber 120 via inlet 128, for example in embodiments wherein the electrolysis comprises oxygen reduction at the cathode and oxygen evolution at the anode. The excess air or oxygen can then be directed out of the electrolysis chamber via outlet 124. The aqueous solution comprising hydrogen peroxide generated in electrolysis chamber 120 can be directed out of electrolysis chamber 120 and into reaction chamber 130 via conduit 126.

Reaction chamber 130 comprises metal catalyst 139, which is shown on a mesh-type catalyst support. However, the metal catalyst may be in any suitable form for a catalyst as described above. Reaction chamber 130 further comprises gas inlet 132, which is operable to supply a natural gas or methane feed into reaction chamber 130. The methane dissolves into the aqueous solution and reacts with hydroxyl radicals (formed by Fenton's reaction between the hydrogen peroxide and a source of ferrous ions) to produce the oxycarbon products via the reaction mechanisms described above. A light source 136 is configured to photoreduce the ferric ions to ferrous ions in the aqueous solution within reaction chamber 130 to regenerate the Fenton's reagents for hydroxyl radical production. In certain embodiments, light source 136 is sunlight, although other sources of light energy may be used, so long as light source 136 provides sufficient energy to photoreduce the ferric ions to ferrous ions. Unreacted methane and/or other gasses are directed out of reaction chamber 130 via gas outlet 138. In certain embodiments, the unreacted methane may be recycled back into reaction chamber 130 via gas inlet 132. The oxycarbon products can then be directed out of reaction chamber 130 and into separation unit 140 via conduit 134. The oxycarbon products may be dissolved or otherwise mixed with the aqueous solution in a liquid state, or one or more of the oxycarbon products may be in a gas state. Thus, it should be understood that reaction chamber 130 may further comprise one or more additional product outlets or other conduits to remove the oxycarbon products and/or direct the products to further separation processes as appropriate.

Separation unit 140 generally comprises product outlet 142 and aqueous solution outlet 144. Separation unit 140 may comprise one or more individual unit operations capable of separating the oxycarbon products from each other and/or from the aqueous solution as desired. For example, in certain embodiments, separation unit 140 comprises one or more distillation columns, absorption or stripping columns, crystallization units, adsorption columns, membrane separation units, and/or extraction units.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth a series of experiments to understand the "over-activation dilemma" in the hydroxyl radical-enabled methane activation in aqueous systems. It is necessary to isolate the methane activation from $H_2O_2$ generation/hydroxyl radical creation, and thus the experimental work was designed to particularly focus on the methane activation. The key information of the experiments is presented in the examples below. It is to be understood, however, that these examples are provided by way of illustration and nothing therein should be taken as a limitation upon the overall scope of the invention.

Example 1

Objective

Hydroxyl radicals can be generated from reduction of hydrogen peroxide by utilizing a reductive agent in an aqueous system. Choice of pH, selection of the reductive ligand, and concentrations of hydrogen peroxide and reductive agent in solution are important consideration. This experiment investigated and established the preferred solution conditions for methane activation.

Methods and Devices

The proton Nuclear Magnetic Resonance (1H NMR) spectroscopy is the major instrumental technique used to study solution conditions by monitoring products produced in reaction solution. The Varian Mercury VX Oxford NMR 300 MHz is the spectrometer used in this study (available in the Chemistry Department at Wichita State University). By properly locking and shimming samples, the spectroscopy can be achieved, and by comparing the known concentration of solute in the solution, it is possible to calculate the concentrations of all other proton-containing compounds.

pH Selection

An acidic environment is generally required to generate hydroxyl radicals, and the typical pH range is from 1.2 to 7.4. Depending on the external supply of hydrogen peroxide, the pH has different impacts on the generation of hydroxyl radicals. Without supplying hydrogen peroxide, increasing pH can enhance hydroxyl-radical production; while with supplying hydrogen peroxide, increasing pH has no significant impact on the production of hydroxyl radicals. In this study, the pH of 3 was chosen for generating hydroxyl radicals for methane activation.

Selection of Fenton's Reagent

In general, hydroxyl radicals are effectively formed via the Fenton process, wherein $Fe^{2+}$ (ferrous) ions are used to catalyze hydrogen peroxide to generate hydroxyl radicals. Since the ferrous ions are eventually consumed in oxidative environment, utilizing UV irradiation to regenerate $Fe^{2+}$ ions from $Fe^{3+}$ ions can be used. Ligands with greater ratio of oxygen to carbon ratio usually possess higher photoreduction ability. In this study, in order to eliminate the doubt over external sources of carbons in our system, both $FeCl_2$ and $FeSO_4$ could have been chosen as the Fenton's reagent, since they are free of any carbon atoms in their ligands. This will make the balance of carbon atoms accurate and straightforward. However, chlorine can be strongly adsorbed on the surface of some transition metals (e.g., Pt and Ag), which causes "surface contamination" that could interfere with the methane upgrading. As such, $FeSO_4$ was chosen over $FeCl_2$ to serve as the Fenton's reagent in this study.

Concentrations of Hydrogen Peroxide and Ferrous Sulfate

In order to simplify the reaction system, only the initial, yet sufficient, concentration of hydrogen peroxide was controlled, since hydrogen peroxide is the only source of hydroxyl radicals. The generation of hydroxyl radicals from hydrogen peroxide is catalyzed by an agent. $FeSO_4$ was used to serve for this need. $FeSO_4$ agent offers one of the highest reaction kinetics among the chain reactions. In this preliminary study, the concentration ratio of $H_2O_2$ to $Fe^{2+}$ ions was investigated, and the preferred concentration ratio was obtained. Higher $D_2O_2$ concentration (e.g., 50 mM) than the optimal one (5 mM) will lead to no product of methane activation, and this is also true for the Fe2+ concentration. The ratio of $[H_2O_2]$ to $[Fe^{2+}]$ is rather important, and thus a range of $[H_2O_2]/[Fe^{2+}]$ ratios were examined: 1, 10, 50 and 200, with different combinations of concentrations. The $[H_2O_2]/[Fe^{2+}]$ ratio of 50 was chosen for the following studies due to the highest product concentration in the same time (2 hours).

Conclusion

The conditions for methane activation in the experimental system are summarized as: pH is adjusted as 3 using $H_2SO_4$; the initial concentration of $Fe^{2+}$ is 0.25 mM, using $FeSO_4$; the initial concentration of $D_2O_2$ is 12.5 mM; and the initial molar ratio of $D_2O_2$ to $Fe^{2+}$ is 50:1.

Example II

Introduction

In order to simplify the reaction system and to better understand the methane activation, the methane upgrading was separated from the hydroxyl radical generation (from $H_2O_2$). Surprisingly, methane activation was not observed using only the solution condition, which is apparently in contradiction with the general understanding in the art. As described below, however, when a piece of metal foil was introduced in the reaction solution, different products of methane activation were obtained. To the inventors' knowledge, such a phenomenon has never been reported or recorded. It is believed that the metal surface plays a key role of "facilitation" that enables the methane activation.

Methodology

The facilitating effect of metal surfaces on the methane activation was studied by testing different metals. The selection of metals was based on the stability against the acidic environment: Platinum, palladium, copper, gold, rhenium, and silver. The relationship between the binding energy of metals with methane and the production rates of activation products was also investigated.

Materials and Reaction Conditions

High-purity $D_2O$ (99.9%) and $FeSO_4$ (99.0%) were from Sigma-Aldrich. The solution of $D_2O_2$ in $D_2O$ (heavy water) with 35 wt. % was from Icon Isotopes; and sulfuric acid (98%) was supplied by Fisher-Scientific Company. Notably, high purity deuterium peroxide and heavy water were used to provide the most accurate experimental environment. However, it should be understood that hydrogen peroxide could also be used to achieve the same or similar results. Very pure methane gas (99.999%) was supplied by Cal Gas Direct Inc. Platinum, copper, gold, rhenium, and silver metal foils were obtained from Alfa, and they have the same foil size of 1 inch square and the same thickness of 25 μm.

Testing Method of Methane Upgrading

For each test, both $D_2O_2$ and $FeSO_4$, were introduced in 12 mL of $D_2O$ solvent. The pH was then accurately set as 3 by adding $H_2SO_4$. The initial concentration of $Fe^{2+}$ was 0.25 mM, and the initial molar ratio of $D_2O_2$ to $Fe^{2+}$ was 50:1 (the $D_2O_2$ concentration: 12.5 mM). The methane gas was introduced to the solution using Teflon tubing at a constant flow rate of 100 mL/min. A thin syringe needle was used to serve as the vent to discharge unused methane and gas products if any. Chances of external contaminations from atmosphere are minimized by tight sealing using a silicon rubber stopper. The whole solution was held in a 50-mL round glass flask with constant magnetic stirring. Before introducing methane gas, the reaction system was stirred for ~10 min to generate hydroxyl radicals. After a certain reaction time, a small amount of reaction solution was sampled for NMR testing. For each 1H NMR sample, 0.7 mL of the reaction solution was inserted into NMR tube. The 1H NMR spectroscopy was obtained with a number of 256 scans for every sample.

Results

Absence of Metal Surface

The experiment was conducted in a 12-hour duration. On each NMR spectrum, there are two sharp peaks: 4.76 ppm as water solvent and 0.18 ppm as the dissolved methane. A wide peak around 3.6 ppm was confirmed to be a signal noise caused by the long-used NMR spectrometer. Clearly, over 12 hours of reaction duration, no product was observed of methane activation.

Platinum

One of the most common metals used as a catalyst in different reactions is Platinum. In this time, a platinum foil (1 inch square in size and 25 μm in thickness) was place in the reaction solution and all other conditions were kept the same. In the NMR, new products emerged in solution and growing along with time: 3.36 ppm which is from $C\underline{H}_3OH$, 3.87 ppm from $HCOOC\underline{H}_3$, and 8.25 ppm from $\underline{H}COOCH_3$ and/or $\underline{H}COOH$. The identifications were verified by matching those pure substances in 1H NMR. The methane activation is so fast in the present of Pt foil that it was possible to detect the activation products in only 5 mins (i.e., 0 hour). Compared with the case in the absence of metal, the presence of a simple platinum foil makes a huge difference for the methane activation under exactly the same test conditions. The most reasonable explanation is that the metal surface serves as a catalyst or a mediator to effectively and critically facilitate the methane activation. The increasing trend of new peaks for reaction products becomes complicated after a couple of hours, which indicates the product evolution and/or decomposition. Table 1 shows the calculated concentrations of each product over time.

TABLE 1

Concentrations of Activation Products with Platinum (Pt).

| Time (hr.) | [CH$_3$OH] (mM) | [HCOOCH$_3$] (mM) | [HCOOH] (mM) |
|---|---|---|---|
| 0 | 0 | 0 | 0 |
| 0.25 | 0.125 | 0.048 | 0.125 |
| 0.5 | 0.130 | 0.144 | 0.130 |
| 1 | 0.135 | 0.154 | 0.350 |
| 2 | 0.106 | 0.163 | 0.427 |
| 4 | 0.134 | 0.206 | 0.643 |
| 6 | 0 | 0.144 | 0.576 |
| 18 | 0 | 0.115 | 0.331 |
| 20 | 0 | 0 | 0.461 |
| 22 | 0 | 0 | 0.374 |
| 23 | 0 | 0 | 0.432 |
| 36 | 0 | 0 | 0 |

Note:
CH$_4$ concentration in solution is considered a constant of 1.44 mM for calculating other concentrations.

For all three activation products, the concentration quickly increase, reaches a maximum value around 5 hours, and then decreases to zero eventually. The maximum concentrations were 0.643 mM, 0.206 mM, and 0.135 mM for formic acid, methyl formate, and methanol. The facilitating effect of the Pt surface is clear.

Palladium

From the same periodic group of platinum, palladium was also tested as well, with all other test conditions unchanged. Similar to the case of Pt, that same three product peaks emerged in the presence of palladium. Table 2, presents the concentration results of methanol, methyl formate, and formic acid in reaction solution.

TABLE 2

Concentrations of Activation Products with Palladium (Pd).

| Time (hr.) | [CH$_3$OH] (mM) | [HCOOCH$_3$] (mM) | [HCOOH] (mM) |
|---|---|---|---|
| 0 | 0 | 0 | 0 |
| 1 | 0.240 | 0.226 | 0.077 |
| 2 | 0.206 | 0.235 | 0.096 |
| 4 | 0.187 | 0.230 | 0.202 |
| 6 | 0.139 | 0.259 | 0.202 |
| 8 | 0.250 | 0.293 | 0.269 |
| 11.25 | 0 | 0.288 | 0.230 |

Note:
CH$_4$ concentration in solution is considered a constant of 1.44 mM for calculating other concentrations.

The concentrations of both methyl formate and formic acid initially increased, reached their peak concentrations at the reaction of 8 hours, and then decreased. The concentration of methanol was a bit complicated, and still it reached the peak value at the same reaction time of 8 hours. The maximum concentrations observed were 0.250, mM, 0.293 mM, and 0.269 mM for methanol, methyl formate, and formic acid, respectively. Compared to the case of Pt, the production rates of using Pd surface were relatively slower, as evidenced by the less peak concentration and/or longer reaction time to reach the peak. This activation result again confirms the facilitating effect from a metal surface.

Copper

As a stable metal from the neighboring periodic group of Pt and Pd, copper was used as the third metal for facilitating the methane activation in our system. Different from Pt and Pd, only one activation product, methyl formate (3.87 ppm), was observed in the case of Cu. Table 3 presents the calculated concentrations of methyl formate in reaction solution.

TABLE 3

Concentrations of Activation Products with Copper (Cu).

| Time (hr.) | [CH$_3$OH] (mM) | [HCOOCH$_3$] (mM) | [HCOOH] (mM) |
|---|---|---|---|
| 0 | 0 | 0 | 0 |
| 0.5 | 0 | 0 | 0 |
| 1 | 0 | 0 | 0 |
| 4 | 0 | 0.134 | 0 |
| 6 | 0 | 1.253 | 0 |
| 8 | 0 | 0.154 | 0 |
| 10 | 0 | 0.437 | 0 |
| 11.75 | 0 | 0.149 | 0 |

Note:
CH$_4$ concentration in solution is considered a constant of 1.44 mM for calculating other concentrations.

The concentration of methyl formate initially increased, reached the peak value, and then decreased eventually. The maximum value of 1.25 mM is obtained and then the same decomposition phenomenon appears for copper as well. Although only one activation product was observed, the results obtained here also confirm the facilitating effect of metal surface.

Gold

From the same periodic group of Cu, Au was studied for facilitating the methane activation as well. The Au behaves much like Pt and Pd in terms of forming three activation products. Table 4 presents the calculated concentrations of methanol, methyl formate and formic acid.

TABLE 4

Concentrations of Activation Products with Gold (Au).

| Time (hr.) | [CH$_3$OH] (mM) | [HCOOCH$_3$] (mM) | [HCOOH] (mM) |
|---|---|---|---|
| 0 | 0 | 0 | 0 |
| 4 | 0.120 | 0.115 | 0 |
| 6 | 0.154 | 0.130 | 0.014 |
| 8 | 0.173 | 0.168 | 0.106 |
| 10 | 0.139 | 0.130 | 0.101 |
| 12 | 0.144 | 0.149 | 0.211 |
| 24 | 0.187 | 0.226 | 0.379 |

Note:
CH$_4$ concentration in solution is considered a constant of 1.44 mM for calculating other concentrations.

Compared to Pt and Pd, the methane activation in the case of gold was relatively slow. In addition, the product concentrations were also low. For instance, the maximum concentration of formic acid reached only 0.37 mM after 24 hours. The small Au foil (1 inch square) was used, and the activation rates were so low that in 24 hours the concentrations of none of three activation products showed the peak value.

To extend the gold available surface area, a gold gauze (25 cm×25 cm) was purchased from Alfa-Aesar Co. with purity of 99.9%. By using a gold gauze instead of gold foil, the available surface area of the metal for methane activation reaction could be increased by factor of 6.34. Table 5 presents the final calculated concentrations of products in reaction solution in presence of gold gauze.

TABLE 5

Concentrations of Activation Products with Gold Gauze (Au).

| Time (hr.) | [CH$_3$OH] (mM) | [HCOOCH$_3$] (mM) | [HCOOH] (mM) |
|---|---|---|---|
| 2 | 0.163 | 0.182 | 0.106 |
| 5 | 0.235 | 0.240 | 0.322 |
| 7 | 0.715 | 1.046 | 0.879 |
| 9 | 0.202 | 0.312 | 0.437 |
| 24 | 0 | 0 | 0.331 |

Note:
CH$_4$ concentration in solution is considered a constant of 1.44 mM for calculating other concentrations.

Rhenium

Rhenium was also tested, due to its stability in acidic environment. Table 6 presents the calculated concentrations of methanol, methyl formate, and formic acid in reaction solution.

TABLE 6

Concentrations of Activation Products with Rhenium (Re).

| Time (hr.) | [CH$_3$OH] (mM) | [HCOOCH$_3$] (mM) | [HCOOH] (mM) |
|---|---|---|---|
| 0 | 0 | 0 | 0 |
| 1.25 | 0 | 0.139 | 0 |
| 2 | 0.221 | 0.187 | 0 |
| 4 | 0.115 | 0.062 | 0.154 |
| 8 | 0.269 | 0.331 | 0 |
| 10.5 | 0.182 | 0.163 | 0.197 |
| 24 | 0.139 | 0 | 0.216 |

Note:
CH$_4$ concentration in solution is considered a constant of 1.44 mM for calculating other concentrations.

The concentration profiles show the peak concentrations: 0.216 mM, 0.269 m M, and 0.332 mM for formic acid, methyl formate, and methanol, respectively.

Silver

The last metal tested was silver that is from the same periodic group of Au and Cu. The methane activation over silver was very fast in the first hour and then all the generated products were decomposed. Same as the case of copper, the only observed activation product was methyl formate. Table 7 presents the calculated concentrations of methyl formate in reaction solution.

TABLE 7

Concentrations of Activation Products with Silver (Ag).

| Time (hr.) | [CH$_3$OH] (mM) | [HCOOCH$_3$] (mM) | [HCOOH] (mM) |
|---|---|---|---|
| 0 | 0 | 0 | 0 |
| 0.25 | 0 | 0.336 | 0 |
| 0.5 | 0 | 0.264 | 0 |
| 1 | 0 | 0.134 | 0 |
| 2 | 0 | 0 | 0 |
| 4 | 0 | 0 | 0 |
| 8 | 0 | 0 | 0 |

Note:
CH$_4$ concentration in solution is considered a constant of 1.44 mM for calculating other concentrations.

The concentration of methyl formate rapidly rises in very beginning of the reaction and reaches its peak value of 0.336 mM in about 15 minutes.

Correlation Between Methane Activation and Metal Binding Energy

In this study, the powerful facilitating effect of metal surfaces on methane activation has been confirmed. And, it has been observed that different metal surfaces result in varying activation rate and different activation products sometimes. It is of particular interest to investigate the underlying parameter that governs the activation kinetics. The best estimate for the generation rate of activation products for each metal surface is to use the very first data collected during each experiment setup. This is due to the fact that after a couple of hours the rather complicated evolution and decomposition of activation products occur when reaction proceeds longer (even over half of an hour). There are three activation products: methanol, methyl formate, and formic acid; and they are different "average oxidation depth" (AOD) on carbon atom: 1, 2, and 3 of AOD for methanol, methyl formate, and formic acid. Note that, here the AOD is defined with the average number of C—O bonds per carbon atom. Based on the AOD values and the experimental observations, methanol should be the earliest activation products, then methyl formate and formic acid. As such, it is proposed that the production of $CH_3OH$ via the following mechanism:

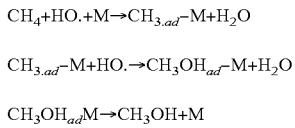

This could be then followed by another series of reaction to generate deeper oxidized products such as formic acid in a mechanism as follows:

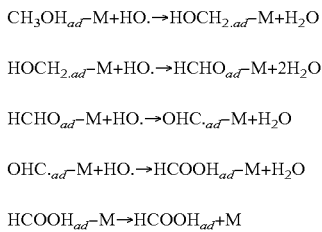

The reactions between products themselves and also between products and hydroxyl radicals present in the reaction solution will make the system more and more complicated. Based on the previous mechanisms, the most reasonable mechanism to generate methyl formate is as follow:

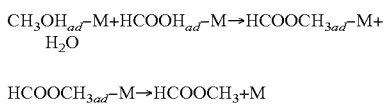

Generation rates of assorted products along with different metal surfaces could be expressed by unit of ($\mu mol\ m^{-2}h^{-1}$). Using the data obtained from 1H NMR spectra, generation rates of $CH_3OH$ and $HCOOCH_3$ oxycarbon products can be estimated with acceptable accuracy. Results from activation rates using different metal surfaces are presented in Table 8.

TABLE 8

Production Rates with Different Metal Surfaces.

| Metal | Methanol ($\mu mol\ m^{-2}\ h^{-1}$) | Methyl formate ($\mu mol\ m^{-2}\ h^{-1}$) |
|---|---|---|
| Platinum | 1290 | 1475 |
| Palladium | 299.5 | 351.4 |
| Copper | 0 | 121.6 |
| Gold | 115.0 | 119.0 |
| Rhenium | 1060 | 1069 |
| Silver | 0 | 0 |

Metal surface area is 0.00125 $m^2$ for all the metals used in experiment.

For $CH_3OH$ product, its generation rate on metal surfaces follows the descending order:

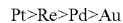

For $HCOOCH_3$ product, its generation rate on metal surfaces follows a similar trend:

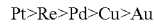

By investigating adsorption energies of some species on metal surfaces, it was found that the $CH_3.-M$ binding strength (with the most stable adsorption sites) follows the same descending order:

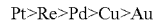

Figure 5:
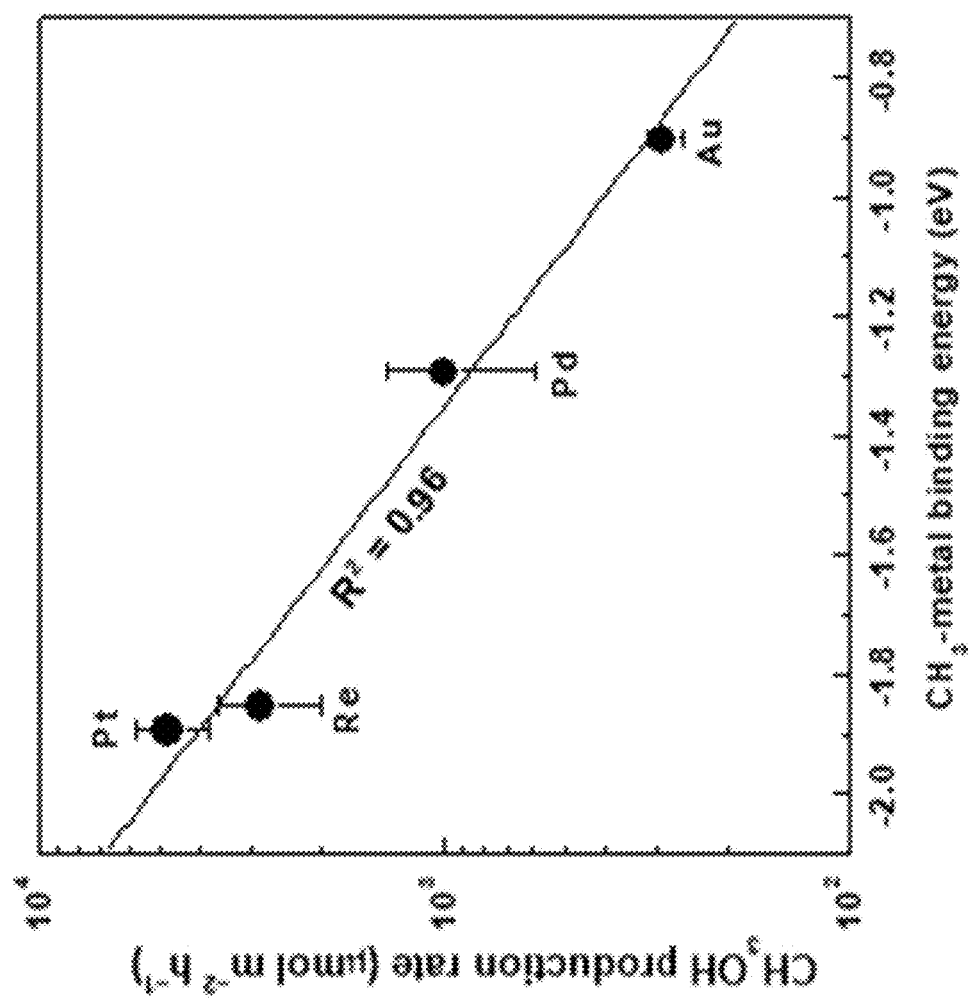
FIG. 5 is a graph showing the correlation between $CH_3OH$ production rate and $CH_3$.-M binding energy with different metals.
Figure 6:
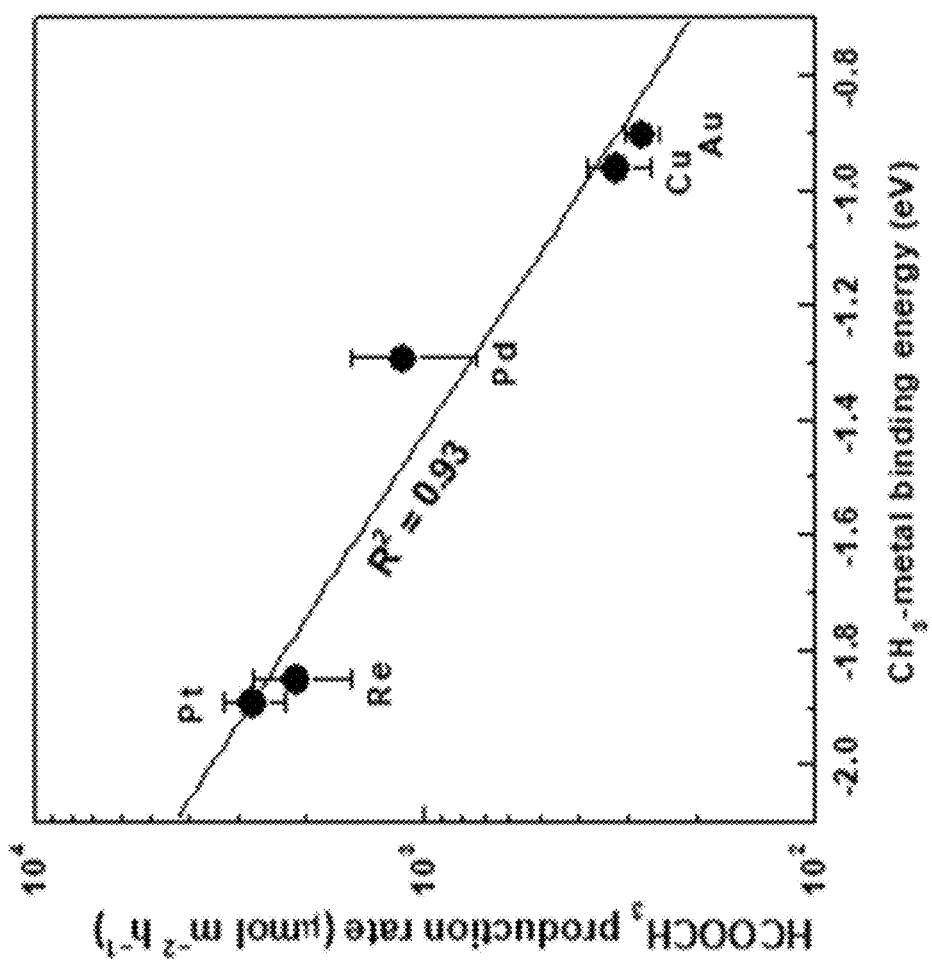
FIG. 6 is a graph showing the correlation between $HCOOCH_3$ production rate and $CH_3$.-M binding energy with different metals.

In addition to the $CH_3.-M$ binding energy, other binding energies were also investigated, including H.-M, O.-M, and HO.-M for the correlation with production rate of oxycarbon products from methane activation, but none of them provides a better correlation. It becomes quite clear that CH3.-M binding energy holds the bottleneck of the methane activation. FIG. 5, shows the correlation between the $CH_3OH$ production rate and the $CH_3.-M$ binding energy for four metal surfaces (Pt, Re, Pd, and Au). Copper is taken out form this chart, since there was no methanol generated by copper surface facilitation. FIG. 6 shows the correlation between $HCOOCH_3$ production rate and the $CH_3.-M$ binding energy for all five metal surfaces (Pt, Re, Pd, Cu, and Au). In fact, the generation rates of both $CH_3OH$ and $HCOOCH_3$ oxycarbon products are similarly following the $CH_3.-M$ binding strength, which quantitatively confirms the facilitation effect of the metal surface for methane activation. The correlation between HCOOH and $CH_3.-M$ binding strength does not show a meaningful relationship. This could be explained by complexity of formic acid generation as other products are constantly getting more oxidized to deeper levels and for formic acid.

Conclusion

Facilitating impact from different metal surfaces on methane activation in reaction solution was studied, with the following reaction conditions: pH=3, $[D_2O_2]$=12.5 mM, $[Fe^{2+}]$=0.25 mM (the ratio $[D_2O_2]/[Fe^{2+}]$=50). Platinum, palladium, copper, gold, rhenium, and silver were tested in the system for the facilitating effect on methane activation. From the 1H NMR spectra of samples for each experiment setup regarding with time, three major products were identified as methanol, methyl formate, and formic acid. The facilitating effect can be reasoned to be that the adsorptions of methyl radicals on metal surfaces have lowered the reaction barrier of C—H bond breaking of methane activation reacting with hydroxyl radicals. Based on the analysis of oxidation depth, the generation mechanisms of the activation products facilitated by metal surfaces have been proposed.

A significant correlation is present between the production rate of methanol and methyl formate and $CH_3.-M$ binding energies. The stronger $CH_3.-M$ binding energy leads to the higher generation rates for methanol and methyl formate. Moreover, this correlation further supports that the metal facilitating effect where the adsorption of $CH_3$. on metal surface indeed lowers the reaction barrier of the C—H bond breaking of methane activation. Also, peak concentrations were observed for all three products. This is due to the complexity of reaction chain and over-oxidation phenomenon of generated products.

The invention claimed is:
1. A method of converting methane to an oxycarbon product, the method comprising:

dissolving methane in an aqueous solution comprising hydroxyl radicals, hydrogen peroxide, and ferrous ions, the aqueous solution comprising a molar concentration ratio of the hydrogen peroxide to the ferrous ions of 1:1 to 200:1; and reacting the methane and hydroxyl radicals in the presence of a metal catalyst having a $CH_3$.–M binding energy of less than 0 eV to produce the oxycarbon product, wherein the metal catalyst comprises a metal selected from the group consisting of platinum, palladium, copper, gold, rhenium, combinations thereof, and alloys thereof.

2. The method of claim 1, wherein the dissolving and/or reacting step is performed under ambient conditions.

3. The method of claim 1, wherein the hydroxyl radicals are produced by Fenton's reaction between the hydrogen peroxide and ferrous ions.

4. The method of claim 3, wherein the Fenton's reaction converts the ferrous ions to ferric ions, the method further comprising photoreducing the ferric ions to ferrous ions.

5. The method of claim 4, wherein the step of photoreducing occurs concurrently with the step of reacting the methane and hydroxyl radicals.

6. The method of claim 1, wherein the hydrogen peroxide is produced by water electrolysis via oxidizing water or reducing oxygen.

7. The method of claim 1, wherein the aqueous solution has a pH of 0 to 6.

8. The method of claim 1, wherein the oxycarbon product comprises one or more of an oxycarbon selected from the group consisting of methanol, methyl formate, formic acid, and mixtures thereof.

9. The method of claim 1, wherein the oxycarbon product is free of carbon monoxide and aldehydes.

10. The method of claim 1, wherein the metal catalyst does not comprise cobalt phthalocyanine.

* * * * *